(12) United States Patent
Bolea et al.

(10) Patent No.: US 9,933,446 B2
(45) Date of Patent: Apr. 3, 2018

(54) PROCESSING OF BIOLOGICAL GROWTH MEDIA BASED ON MEASURED MANUFACTURING CHARACTERISTICS

(75) Inventors: Phillip A. Bolea, Grant, MN (US); Michael E. Hughes, Burnsville, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1339 days.

(21) Appl. No.: 12/920,188

(22) PCT Filed: Feb. 27, 2009

(86) PCT No.: PCT/US2009/035438
§ 371 (c)(1),
(2), (4) Date: Mar. 8, 2011

(87) PCT Pub. No.: WO2009/111298
PCT Pub. Date: Sep. 11, 2009

(65) Prior Publication Data
US 2011/0153220 A1    Jun. 23, 2011

Related U.S. Application Data

(60) Provisional application No. 61/033,606, filed on Mar. 4, 2008.

(51) Int. Cl.
*G01N 35/00* (2006.01)

(52) U.S. Cl.
CPC .......... *G01N 35/00732* (2013.01); *G01N 2035/00752* (2013.01); *G01N 2035/00851* (2013.01)

(58) Field of Classification Search
None
See application file for complete search history.

(56) References Cited

U.S. PATENT DOCUMENTS

| | | | |
|---|---|---|---|
| 3,493,772 A | 2/1970 | Daughters |
| 3,745,090 A | 7/1973 | Chappelle |
| | (Continued) | |

FOREIGN PATENT DOCUMENTS

| | | |
|---|---|---|
| DE | 19819144 | 6/2000 |
| EP | 0008826 | 3/1980 |
| | (Continued) | |

OTHER PUBLICATIONS

Lopes, "Chemometrics in bioprocess engineering: process analytical technology (PAT) applications," Chemometrics and Intelligent Laboratory Systems, vol. 74, p. 269-275, 2004.*

(Continued)

*Primary Examiner* — G. Steven Vanni

(57) ABSTRACT

This disclosure is directed to information management techniques that may be used during automated processing of biological growth media. In one embodiment, a method comprises reading an identification element associated with a biological growth medium, identifying manufacturing information associated with the biological growth medium based on the identification element, wherein the manufacturing information includes one or more manufacturing variables measured from the biological growth medium when the biological growth medium was manufactured, adjusting one or more processing parameters associated with processing of the biological growth medium based on the manufacturing variables measured from the biological growth medium when the biological growth medium was manufactured, and processing the biological growth medium in an automated system based on the processing parameters.

13 Claims, 8 Drawing Sheets

(56) References Cited

U.S. PATENT DOCUMENTS

| | | | |
|---|---|---|---|
| 3,811,036 | A | 5/1974 | Perry |
| 3,962,040 | A | 6/1976 | Campbell |
| 4,118,280 | A | 10/1978 | Charles |
| 4,146,775 | A | 3/1979 | Kirchner |
| 4,160,601 | A | 7/1979 | Jacobs |
| 4,353,988 | A | 10/1982 | Couse |
| 4,563,096 | A | 1/1986 | Chidlow |
| 4,591,567 | A | 5/1986 | Britten |
| 4,637,053 | A | 1/1987 | Schalkowsky |
| 4,672,598 | A | 6/1987 | Koken |
| 4,720,463 | A | 1/1988 | Farber |
| 4,724,215 | A | 2/1988 | Farber |
| 4,817,785 | A | 4/1989 | Farber |
| 4,856,073 | A | 8/1989 | Farber |
| 4,952,976 | A | 8/1990 | Katoh |
| 5,099,521 | A | 3/1992 | Kosaka |
| 5,117,467 | A | 5/1992 | Misaki |
| 5,202,010 | A | 4/1993 | Guzman |
| 5,268,966 | A | 12/1993 | Kasdan |
| 5,270,173 | A | 12/1993 | Yonemori |
| 5,290,701 | A | 3/1994 | Wilkins |
| 5,329,686 | A | 7/1994 | Kildal |
| 5,364,766 | A | 11/1994 | Mach |
| 5,366,873 | A | 11/1994 | Eden |
| 5,372,485 | A | 12/1994 | Sumser |
| 5,372,936 | A | 12/1994 | Fraatz |
| 5,375,043 | A | 12/1994 | Tokunaga |
| 5,403,722 | A | 4/1995 | Floeder |
| 5,428,690 | A | 6/1995 | Bacus |
| 5,448,652 | A | 9/1995 | Vaidyanathan |
| 5,491,567 | A | 2/1996 | Morikawa |
| 5,510,246 | A | 5/1996 | Morgan |
| 5,539,517 | A | 7/1996 | Cabib |
| 5,573,950 | A | 11/1996 | Graessle |
| 5,591,974 | A | 1/1997 | Troyer |
| 5,635,367 | A * | 6/1997 | Lund ............................... 435/34 |
| 5,671,290 | A | 9/1997 | Vaidyanathan |
| 5,694,478 | A | 12/1997 | Braier |
| 5,721,435 | A | 2/1998 | Troll |
| 5,723,308 | A | 3/1998 | Mach |
| 5,744,322 | A | 4/1998 | Krejcarek |
| 5,747,333 | A | 5/1998 | Jungmann-Campello |
| 5,781,311 | A | 7/1998 | Inoue |
| 5,787,189 | A | 7/1998 | Lee |
| 5,805,404 | A | 9/1998 | Kane |
| 5,808,284 | A | 9/1998 | Domanik |
| 5,817,475 | A | 10/1998 | Gibbs |
| 5,817,508 | A | 10/1998 | Berndt |
| 5,956,158 | A | 9/1999 | Pinzarrone |
| 5,995,645 | A | 11/1999 | Soenksen |
| 6,002,789 | A | 12/1999 | Olsztyn |
| 6,058,209 | A | 5/2000 | Vaidyanathan |
| 6,063,590 | A | 5/2000 | Brenner |
| 6,096,272 | A | 8/2000 | Clark |
| 6,107,054 | A | 8/2000 | Gibbs |
| 6,134,354 | A | 10/2000 | Lee |
| 6,189,839 | B1 | 2/2001 | Lemieux |
| 6,215,894 | B1 | 4/2001 | Zeleny |
| 6,238,076 | B1 | 5/2001 | Pascale |
| 6,238,879 | B1 | 5/2001 | Gibbs |
| 6,243,486 | B1 | 6/2001 | Weiss |
| 6,252,979 | B1 | 6/2001 | Lee |
| 6,271,022 | B1 | 8/2001 | Bochner |
| 6,319,668 | B1 | 11/2001 | Nova |
| 6,372,485 | B1 | 4/2002 | Clark |
| 6,375,335 | B1 | 4/2002 | Tabata |
| 6,381,353 | B1 | 4/2002 | Weiss |
| 6,418,180 | B1 | 7/2002 | Weiss |
| 6,459,994 | B1 | 10/2002 | Parekh |
| 6,485,979 | B1 | 11/2002 | Kippenhan |
| 6,488,890 | B1 | 12/2002 | Kirckof |
| 6,583,791 | B2 | 6/2003 | Berryman |
| 6,623,142 | B1 | 9/2003 | Lippmann |
| 6,642,953 | B1 | 11/2003 | Nieto Velasco |
| 6,673,315 | B2 | 1/2004 | Sheridan |
| 6,685,327 | B2 | 2/2004 | Dörrie |
| 6,690,470 | B1 | 2/2004 | Baer |
| 6,711,283 | B1 | 3/2004 | Soenksen |
| 6,716,588 | B2 | 4/2004 | Sammak |
| 6,737,266 | B1 | 5/2004 | Wicks |
| 6,999,607 | B1 | 2/2006 | Kiros |
| 7,057,721 | B2 | 6/2006 | Gardner |
| 7,298,885 | B2 | 11/2007 | Green |
| 7,298,886 | B2 | 11/2007 | Plumb |
| 7,319,031 | B2 | 1/2008 | Vent |
| 7,351,574 | B2 | 4/2008 | Vent |
| 7,496,225 | B2 | 2/2009 | Graessle |
| 7,738,689 | B2 | 6/2010 | Plumb |
| 7,865,008 | B2 | 1/2011 | Graessle |
| 7,901,933 | B2 | 3/2011 | Green |
| 7,957,575 | B2 | 6/2011 | Plumb |
| 8,256,381 | B2 | 9/2012 | Pratt |
| 2001/0031502 | A1 | 10/2001 | Watson |
| 2001/0041347 | A1 | 11/2001 | Sammak |
| 2002/0025082 | A1 | 2/2002 | Kushikkar |
| 2002/0064867 | A1 | 5/2002 | Clark |
| 2002/0137091 | A1 | 9/2002 | Luttermann |
| 2002/0159002 | A1 | 10/2002 | Chang |
| 2002/0167161 | A1 | 11/2002 | Butland |
| 2002/0191825 | A1 | 12/2002 | Parekh |
| 2003/0016406 | A1 | 1/2003 | Hoshino |
| 2004/0032659 | A1 | 2/2004 | Drinkwater |
| 2004/0071342 | A1 | 4/2004 | Locht |
| 2004/0101189 | A1 | 5/2004 | Green |
| 2004/0101951 | A1 | 5/2004 | Vent |
| 2004/0101952 | A1 | 5/2004 | Vent |
| 2004/0101954 | A1 | 5/2004 | Graessle |
| 2004/0102903 | A1 | 5/2004 | Graessle |
| 2005/0053265 | A1 | 3/2005 | Graessle |
| 2005/0053266 | A1 | 3/2005 | Plumb |
| 2005/0095665 | A1 | 5/2005 | Williams |
| 2005/0185178 | A1 | 8/2005 | Gardner |
| 2005/0222778 | A1 | 10/2005 | Levinson |
| 2006/0263258 | A1 | 11/2006 | Harris |
| 2008/0003562 | A1 | 1/2008 | Plumb |
| 2010/0232660 | A1 | 9/2010 | Graessle |
| 2010/0266192 | A1 | 10/2010 | Plumb |
| 2010/0330610 | A1 | 12/2010 | Green |
| 2011/0158499 | A1 | 6/2011 | Bolea |

FOREIGN PATENT DOCUMENTS

| | | | |
|---|---|---|---|
| EP | 0193385 | 9/1986 | |
| EP | 0088601 | 4/1987 | |
| EP | 0301600 | 2/1989 | |
| EP | 0429030 | 5/1991 | |
| EP | 0547709 | 6/1993 | |
| EP | 0397256 | 3/1994 | |
| EP | 0 637 750 | 2/1995 | |
| EP | 0819930 | 1/1998 | |
| EP | 1074610 | 2/2001 | |
| EP | 1172831 | 1/2002 | |
| EP | 0895086 | 11/2004 | |
| GB | 2249829 | 5/1992 | |
| JP | 62-215383 | 9/1987 | |
| JP | 10-24283 | 1/1989 | |
| JP | 5-249105 | 9/1993 | |
| JP | 60-83597 | 3/1994 | |
| JP | 6-98220 | 4/1994 | |
| JP | 6-109545 | 4/1994 | |
| JP | 06-281553 | 10/1994 | |
| JP | 7-275200 | 10/1995 | |
| JP | 9-187270 | 7/1997 | ............. C12M 1/34 |
| JP | 9-509047 | 9/1997 | |
| JP | 10-500302 | 1/1998 | |
| JP | 10-510072 | 9/1998 | |
| JP | 11-500648 | 1/1999 | |
| JP | 2000-270840 | 10/2000 | |
| JP | 2001-242082 | 9/2001 | |
| JP | 2001-525162 | 12/2001 | |
| JP | 2002-510387 | 4/2002 | |
| JP | 2002-538440 | 11/2002 | |
| JP | 2006-507837 | 9/2006 | ............. C12M 1/00 |
| KR | 2002-34171 | 5/2002 | |

(56) References Cited

FOREIGN PATENT DOCUMENTS

| | | | | |
|---|---|---|---|---|
| WO | WO 1991-06911 | 5/1991 | | |
| WO | WO 1992-12233 | 7/1992 | | |
| WO | WO 1994-01528 | 1/1994 | | |
| WO | WO 1994-26926 | 11/1994 | | |
| WO | WO 1995-16768 | 6/1995 | | |
| WO | WO 1995-31732 | 11/1995 | | |
| WO | WO 1996-18167 | 6/1996 | | |
| WO | WO 1996-18721 | 6/1996 | | |
| WO | WO 1997-15229 | 5/1997 | | |
| WO | WO 1998-53301 | 11/1998 | | |
| WO | WO 1998-59314 | 12/1998 | | |
| WO | WO 1999-28436 | 6/1999 | | |
| WO | WO 2000-32807 | 6/2000 | | |
| WO | WO 2000-49129 | 8/2000 | | |
| WO | WO 2000-49130 | 8/2000 | | |
| WO | WO 2000-51058 | 8/2000 | | |
| WO | WO 2000-65094 | 11/2000 | | |
| WO | WO 2001-04828 | 1/2001 | | |
| WO | WO 2001-09371 | 2/2001 | | |
| WO | WO 2001/38559 | 5/2001 | ............... | C12Q 1/00 |
| WO | WO 2001-83673 | 11/2001 | | |
| WO | WO 2002-37938 | 5/2002 | | |
| WO | WO 2002-38724 | 5/2002 | | |
| WO | WO 2002-46354 | 6/2002 | | |
| WO | WO 2002-066961 | 8/2002 | | |
| WO | WO 2002-090966 | 11/2002 | | |
| WO | WO 2003-014400 | 2/2003 | | |
| WO | WO 2003-038413 | 5/2003 | | |
| WO | WO 2004/051554 | 6/2004 | ............... | G06K 9/00 |
| WO | WO 2009-111301 | 9/2009 | | |

OTHER PUBLICATIONS

Clemmensen, "A method for comparison of growth media in objective identification of Penicillium based on multi-spectral imaging," J Microbiological Methods, vol. 69, p. 249-255, 2007.*

Corkidi, G. et al.; "COVASIAM: an Image Analysis Method That Allows Detection of Confluent Microbial Colonies and Colonies of Various Sizes for Automated Counting"; Applied and Environmental Microbiology; vol. 64, No. 4, 1998 pp. 1400-1404.

Gilchrist, J.E. et al; "Spiral Plate Method for Bacterial Determination"; Applied Microbiology; vol. 25, No. 2; 1973; pp. 244-252.

Kalasinsky, K. et al.; "Raman Chemical Imaging Spectroscopy Reagentless Detection and Identification of Pathogens: Signature Development and Evaluation"; Analytical Chemistry; vol. 79, No. 7; 2007; pp. 2658-2673.

Product Brochure entitled "Petrifilm™ Information Management System—Reduce Operational Costs and Increase Productivity"; 3M Microbiology Products; 1999; 70-2009-1996-0 (3 pgs.).

Serebriiskii, I. et al; Short Technical Reports entitled "Streamlined Yeast Colorimetric Reporter Activity Assays Using Scanners and Plate Readers," BioTechniques, vol. 29, No. 2, 2000, pp. 278-288.

Wright, K.M. et al.; "Determination of mean growth parameters of bacterial colonies immobilized in gelatin gel using a laser gel-cassette scanner"; International Journal of Food Microbiology; vol. 57; 2000; pp. 75-89.

Marotz, J. et al.; "Effective object recognition for automated counting of colonies in Petri dishes (automated colony counting)"; Computer Methods and Programs in Biomedicine; vol. 66; 2001; pp. 183-198.

* cited by examiner

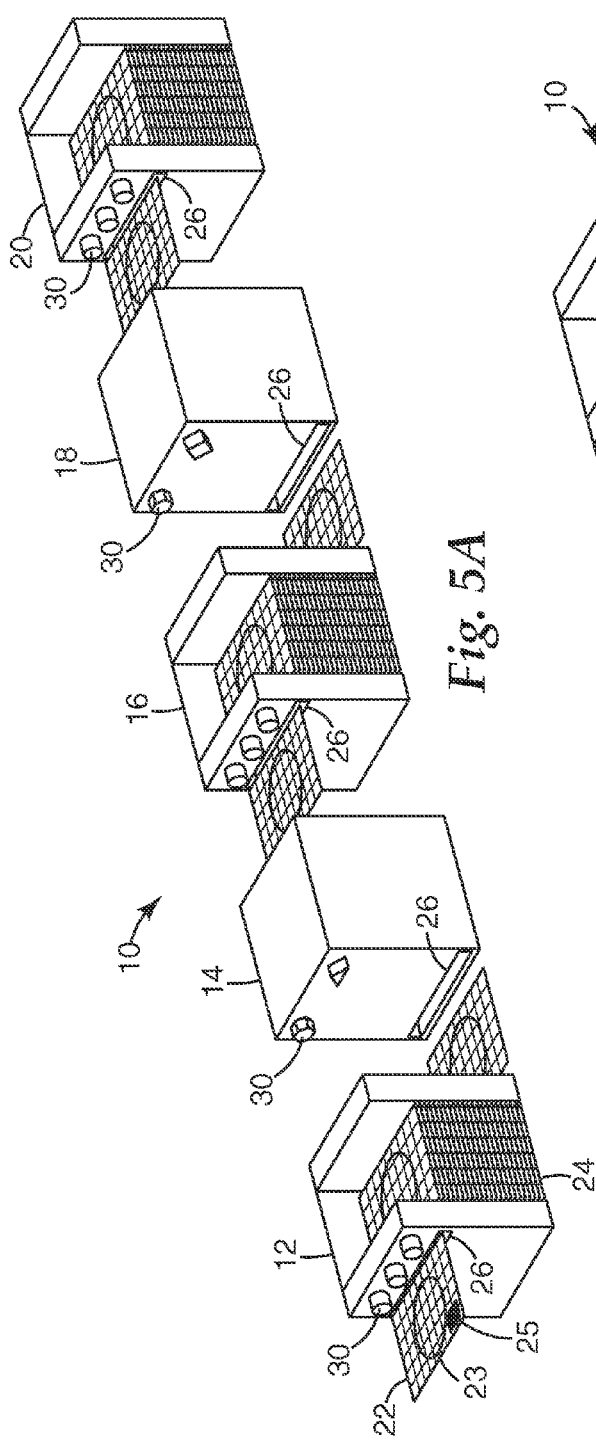
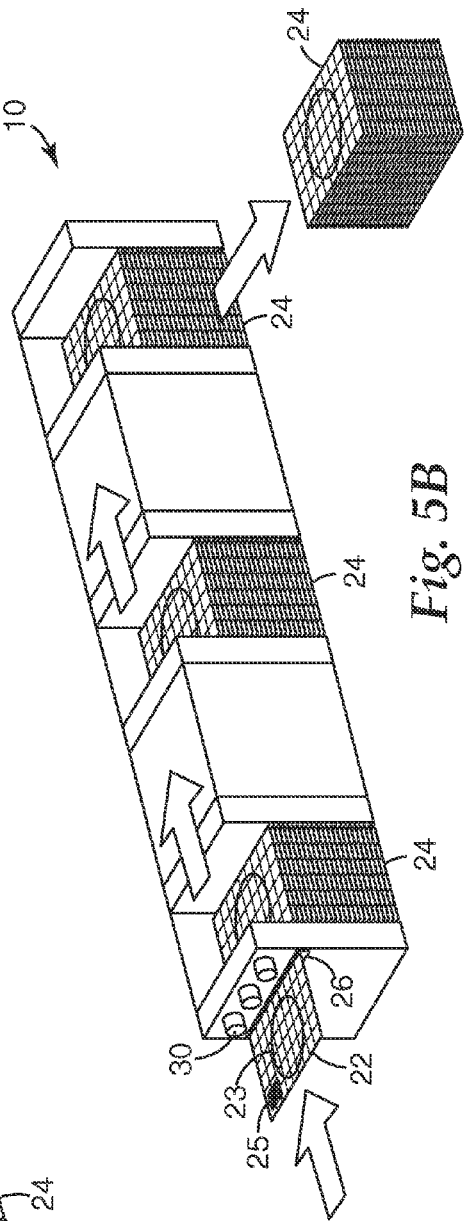

PROCESSING OF BIOLOGICAL GROWTH MEDIA BASED ON MEASURED MANUFACTURING CHARACTERISTICS

CROSS REFERENCE TO RELATED APPLICATIONS

This application claims the benefit of U.S. Provisional Application Ser. No. 61/033,606, filed Mar. 4, 2008, which is incorporated herein by reference.

FIELD

The invention relates to biological growth media used to analyze bacteria or other biological agents in food samples, laboratory samples, and the like, and to automated systems used to process such biological growth media.

BACKGROUND

Biological safety is a paramount concern in modern society. Testing for biological contamination in foods or other materials has become an important and sometimes mandatory requirement for developers and distributors of food products. Biological testing is also used to identify bacteria or other agents in laboratory samples such as blood samples taken from medical patients, laboratory samples developed for experimental purposes, and other types of biological samples. Various techniques and devices can be utilized to improve biological testing and to streamline and standardize the biological testing process.

In particular, a wide variety of biological growth media have been developed. As one example, biological growth media in the form of growth plates have been developed by 3M Company (hereafter "3M") of St. Paul, Minn. Biological growth plates are sold by 3M under the trade name PETRIFILM plates. Biological growth plates can be utilized to facilitate the rapid growth and detection or enumeration of bacteria or other biological agents commonly associated with food contamination, including, for example, aerobic bacteria, *E. coli*, coliform, *Enterobacteriaceae* species, yeast, mold, *Staphylococcus aureus*, *Listeria* species, *Campylobacter* species, and other biological agents. The use of PETRIFILM plates, or other biological growth media, can simplify bacterial testing of food samples.

Biological growth media can be used to identify the presence of bacteria so that corrective measures can be performed (in the case of food testing) or proper diagnosis can be made (in the case of medical use). In other applications, biological growth media may be used to rapidly grow bacteria or other biological agents in laboratory samples, e.g., for experimental purposes.

Biological growth medium processing systems refer to systems used to process biological growth media, and read or count bacterial colonies, or the amount of a particular biological agent on or in a biological growth medium. For example, a food sample or laboratory sample can be placed on or in a biological growth medium, and then the medium can be inserted into an incubation chamber. After incubation, the biological growth medium can be introduced into the biological reader, which generates one or more images of the biological growth medium. The images can then be analyzed, e.g., via a computer, for automated enumeration of bacterial growth. In this way, biological growth medium processing systems automate the detection and enumeration of bacteria or other biological agents on a biological growth medium, and thereby improve the biological testing process by reducing human error.

SUMMARY

In general, this disclosure is directed to information management techniques that can improve automated processing of biological growth media. The techniques may use a computer database that stores information associated with different biological growth media. This disclosure sets forth different types of information that can be defined or measured for different biological media, and used during various stages of automated processing of the biological growth media. Such information can be associated with different biological media via one or more identification elements (such as one or more bar codes or RFID tags), and tracked via automated techniques. In this way, an automated system for reading biological growth media can be improved.

In one embodiment, this disclosure provides a method comprising reading an identification element associated with a biological growth medium, identifying manufacturing information associated with the biological growth medium based on the identification element, wherein the manufacturing information includes one or more manufacturing variables measured from the biological growth medium when the biological growth medium was manufactured, adjusting one or more processing parameters associated with processing of the biological growth medium based on the manufacturing variables measured from the biological growth medium when the biological growth medium was manufactured, and processing the biological growth medium in an automated system based on the processing parameters.

In another embodiment, this disclosure provides a system comprising an identification element reader that reads an identification element associated with a biological growth medium, a computer that identifies manufacturing information associated with the biological growth medium based on the identification element, wherein the manufacturing information includes one or more manufacturing variables measured from the biological growth medium when the biological growth medium was manufactured, wherein the computer adjusts one or more processing parameters associated with processing of the biological growth medium based on the manufacturing variables measured from the biological growth medium when the biological growth medium was manufactured, and one or more processing units that process the biological growth medium.

In another embodiment, this disclosure provides a system comprising means for reading an identification element associated with a biological growth medium, means for identifying manufacturing information associated with the biological growth medium based on the identification element, wherein the manufacturing information includes one or more manufacturing variables measured from the biological growth medium when the biological growth medium was manufactured, means for adjusting one or more processing parameters associated with processing of the biological growth medium based on the manufacturing variables measured from the biological growth medium when the biological growth medium was manufactured, and means for processing the biological growth medium in an automated system based on the processing parameters.

In another embodiment, this disclosure provides a computer-readable medium comprising instructions that upon execution in a computer of a biological growth medium processing system cause the computer to receive a reading of an identification element read from a biological growth medium identify manufacturing information associated with the biological growth medium based on the identification element, wherein the manufacturing information includes one or more manufacturing variables measured from the biological growth medium when the biological growth medium was manufactured, adjust one or more processing parameters associated with processing of the biological growth medium based on the manufacturing variables measured from the biological growth medium when the biological growth medium was manufactured, and cause the system to process the biological growth medium based on the processing parameters.

Additional details of these and other embodiments are set forth in the accompanying drawings and the description below. Other features, objects and advantages will become apparent from the description and drawings, and from the claims.

BRIEF DESCRIPTION OF DRAWINGS

FIGS. 5A and 5B are perspective illustrations of one exemplary embodiment of a modular processing system capable of implementing one or more of the techniques described in this disclosure.

DETAILED DESCRIPTION

Figure 1:
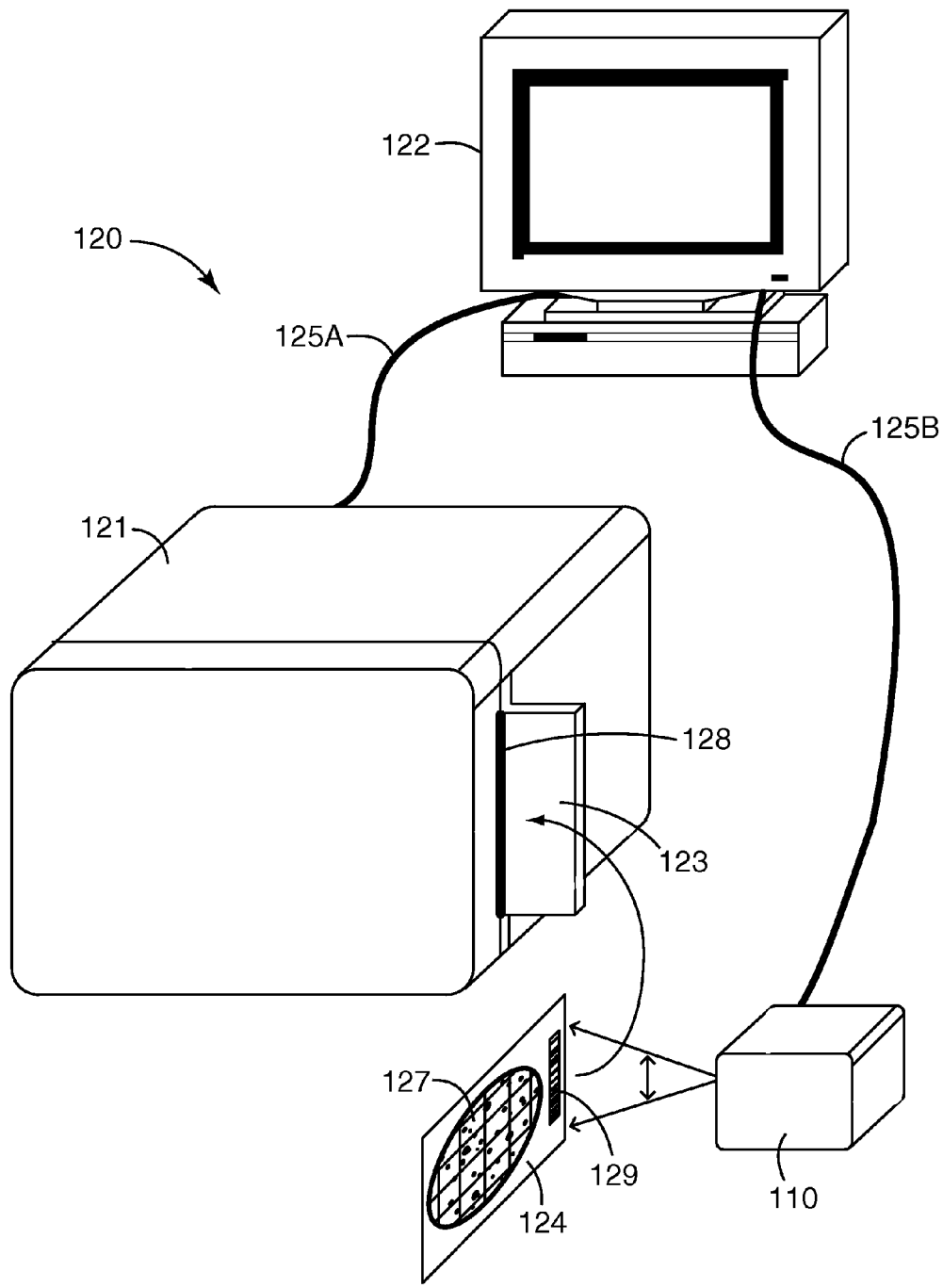
FIG. 1 is a perspective view of an exemplary biological growth medium processing system capable of implementing one or more of the techniques described herein during the processing of a biological growth medium.

This disclosure is directed to information management techniques that may be used during automated processing of biological growth media. The techniques may use a computer database that stores information associated with different biological growth media. This disclosure sets forth different types of information that can be defined or measured for different biological media. The different types of information may be used during various stages of automated processing of the biological growth media. Such information can be associated with different biological media via one or more identification elements of the media (such as one or more bar codes or RFID tags), and the information can be tracked via automated techniques. In this way, an automated system for reading biological growth media can be improved. Similar automated systems are disclosed in U.S. Patent Application No. 61/033,620, filed Mar. 4, 2008 and entitled "INFORMATION MANAGEMENT IN AUTOMATED PROCESSING OF BIOLOGICAL GROWTH MEDIA", which herein is incorporated by reference in its entirety.

In one example, this disclosure provides for the use of manufacturing information associated with a biological growth medium in order to adjust one or more processing parameters during the processing of the biological growth medium. Manufacturing information may be associated with a biological growth medium via an identification element of the biological growth medium. The identification element may comprise a bar code, a radio frequency identification (RFID) tag, or other type of, element, circuit, tag or mechanical features like notches, slots, holes, or indicia use to code information associated with a product or device. In some case, multiple identification elements are used on a given biological growth medium.

According to this disclosure, the manufacturing information includes one or more manufacturing variables measured from the biological growth medium when the biological growth medium was manufactured. The manufacturing variables measured at the time the biological growth medium was manufactured can be used to adjust one or more processing parameters during the processing of the biological growth medium. For example, one or more parameters of a biological reader may be adjusted based on the manufacturing variables, and images of the biological growth medium may be generated by the biological reader. In some cases, biological agents formed on the biological growth medium may be counted by the biological reader based on the images. Alternatively, a separate computer may be used for the image analysis of the images generated by the biological reader. In either case, one or more parameters associated with image analysis of the biological growth medium may be adjusted based on the manufacturing variables measured from the biological growth medium. These or other parameters of a biological growth medium processing system may be adjusted to account for manufacturing variations in media, or manufacturing differences associated with different suppliers of the different components that are used to manufacture biological growth media.

The manufacturing variables measured from the biological growth medium may comprise one or more spectroscopy measurements measured from the biological growth medium when the biological growth medium was manufactured, such as spectroscopy absorption measurements and/or spectroscopy transmission measurements. These types of spectroscopy measurements may be used to tune or adjust the biological reader, e.g., by adjusting the illumination sources, illumination angles, or camera exposures used for generating images of the biological growth medium, or by adjusting algorithms used to count biological agents from such images. For example, spectroscopy measurements associated with media at the time of manufacture may be used to normalize the expected color values associated with the background color of biological growth media. In this case, the spectroscopy measurements may be applied by a computer that analyzes images produced by a biological reader in order to normalize the expected color values.

As yet another example, the manufacturing variables measured from the biological growth medium when the biological growth medium was manufactured may comprise direct measurements of background color of the biological growth medium. These types of measurements may also be used to tune or adjust the biological reader, e.g., by adjusting the illumination sources, illumination angles, or camera exposures used when generating images of the biological growth medium, or by adjusting algorithms used by the biological reader, or by a separate computer to count biological agents from such images.

Other types of manufacturing information that may be associated with the identification element may comprise information such as a plate type associated with the biological growth medium, a manufacturing date associated with the biological growth medium, a manufacturing lot code associated with the biological growth medium, a manufacturer of the biological growth medium. This information may also be used during the processing of the biological growth medium, and may supplement the manufacturing information that is measured from the biological growth medium when the biological growth medium was manufactured. Such manufacturing information may also be used to authenticate a biological growth medium as being provided by a known and reliable company and that the biological growth medium will behave in an expected manner, which can help to ensure quality control during biological testing. Raw materials may change over time, and some attributes of biological growth media may be random or uncontrollable, yet discoverable or measurable after the manufacturing process. The techniques of this disclosure measure such attributes of biological growth media, and use the measurements to improve the automated processing of biological growth media.

Furthermore, in addition to manufacturing information, this disclosure also proposes the use of other types of information in the processing of biological growth media. For example, this disclosure also proposes the use of sample information related to a sample being tested by the biological growth medium. In this case, the identification element (or multiple identification elements) of the biological growth medium may be linked to manufacturing information associated with the biological growth medium, and to sample information related to a sample being tested on the specific biological growth medium.

For example, an identification element reader may read one or more identification elements associated with a biological growth medium, and a computer may identify manufacturing information related to the biological growth medium based on the one or more identification elements of the biological growth medium, and identify sample information related to a sample being tested by the biological growth medium based on one or more identification elements of the biological growth medium. The biological reader generates images of the biological medium, which can then be analyzed for automated counting of biological agents formed on or in the biological growth medium. A computer that performs this image analysis generates a count value for the biological growth medium. The computer then associates the manufacturing information, the sample information and the count value with the one or more identification elements of the biological growth medium.

As examples, the sample information may include a type of sample being tested on the biological growth medium, information about a dilution agent used with the sample, and/or an origin associated with the sample being tested on the biological growth medium. In addition, the sample information may comprise an incubation time associated with a sample inoculated on a biological growth medium. In some cases, at least some of the sample information may be recorded when the count value is generated. This type of recorded sample information may include such things as a date that the count value is generated, and a technician associated with the one or more of the processing steps (e.g., Technician "A" inoculated the biological growth medium and Technician "B" counted the biological growth medium.

Furthermore, in addition to manufacturing information and sample information, the system may also define service information. The service information may comprise information about the biological growth medium processing system, which may be defined and used by service technicians in order to service the system. As examples, the service information may comprise counting rules applied by the computer that performs image analysis, a temperature associated with incubation of the biological medium in an incubator of the biological growth medium processing system, a difference between the count value and a human count, information indicative of human intervention with the biological growth medium processing system during the processing of the biological growth medium, ambient conditions in proximity to the biological reader when images are generated by the biological reader, or other service-type information associated with any devices or units in the system that may be useful to a service technician.

FIG. 1 is a perspective view of an exemplary biological growth medium processing system 120 capable of implementing one or more of the techniques described herein during the processing of biological growth medium 124. Biological growth medium processing system 120 comprises a biological reader 121 coupled to a computer 122. Biological growth medium processing system 120 also includes an identification element reader 110 that reads identification element 129 associated with biological growth medium 124. Computer 122 may perform various techniques for identifying, defining and/or associating information related to the manufacturing and processing of biological growth medium 124. Computer 122 may include memory and may create an information database in its memory to track and store such information. Computer 122 may associate various types of information with identification element 129. Of course, the techniques of this disclosure may also be used in embodiments in which identification element 129 stores all of the information associated with biological growth medium 124, but in this case, identification element 129 may need substantial storage capacity. Identification element 129 may achieve such substantial storage capacity by implementation as a high storage capacity RFID tag with a memory circuit. In certain embodiments, however, identification element 129 may serve as a pointer to information stored in memory of computer 122.

In general, identification element 129 may contain enough storage capacity to enable unique identification of biological growth medium 124. However, multiple identification elements may be used in some embodiments, and in this case, information from a plurality of identification elements may be concatenated to form a unique pointer for biological growth medium 124. Furthermore, as outlined in greater detail below, multiple identification elements may be used to code different types of information, possibly at different times over the life and use of biological growth medium 124. Numerical values associated with one or more identification elements may be analyzed by computer 122 (e.g., via check sum techniques or other data verification techniques). Such analysis may be used to check for robustness and/or proprietary features associated with biological growth medium 124. Furthermore, in some cases, the processing of biological growth medium 124 may be recorded and linked to identification element 129 in order to create a legally traceable record for biological growth medium 124 and the processing that is performed with respect to biological growth medium 124.

In some examples, computer 122 may also perform imaging analysis of the images generated by biological reader 121. However, although computer 122 and biological reader 121 are illustrated as separate units, the techniques of this disclosure could also be implemented by a fully integrated system or device in which a biological reader and the computer are incorporated into a common device. Furthermore, as explained in greater detail below, the techniques of this disclosure could also be used in a modular system that includes one or more biological readers, incubation units, inoculation units, identification element readers, identification element labelers, or other devices that operate in a modular processing pipeline. In addition, although biological reader 121 and identification element reader 110 are illustrated as separate units, identification element reader 110 could be implemented within biological reader 121 such that identification element 129 is read when biological growth medium 124 is received by biological reader 121.

Computer 122 may include a microprocessor that executes software for image analysis of biological growth medium 124, and for database management consistent with the techniques described herein. Accordingly, computer 122 may also include memory to store the various types of information associated with identification element 129. Computer 122 may comprise a personal computer (PC), desktop computer, laptop computer, handheld computer, workstation, or the like. For example, software programs can be loaded on computer 122 to facilitate image analysis of images of biological growth medium 124 generated by biological growth medium processing system 120, and to execute the techniques of this disclosure in which various information associated with identification element 129 is defined and/or used during the processing of biological growth medium 124.

In the example of FIG. 1, biological reader 121 is coupled to computer 122 via interface 125A and identification element reader 110 is coupled to computer 122 via interface 125B. Interfaces 125A and 125B, for example, may comprise a Universal Serial Bus (USB) interface, a Universal Serial Bus 2 (USB2) interface, an IEEE 1394 FireWire interface, a Small Computer System Interface (SCSI) interface, an Advance Technology Attachment (ATA) interface, a serial ATA interface, a Peripheral Component Interconnect (PCI) interface, a serial or parallel interface, or the like.

As illustrated, biological reader 121 is designed to receive a biological growth medium 124. In particular, biological reader 121 includes a housing that defines an input slot 128 for receiving biological growth medium 124. A guide mechanism 123 may be formed on the housing to aid insertion of biological growth medium 124 into biological reader 121. Biological reader 121 also includes an ejection slot (not shown), through which biological growth medium 124 is ejected following imaging of biological growth medium 124. Biological reader 121 may also include other features, such as a display screen (not shown) to display the progress or results of analysis of the biological growth plate to a user.

Biological reader 121 houses an imaging device, such as a 2-dimensional monochromatic camera for generating one or more monochromatic images of an inserted biological growth medium 124. In addition, biological reader 121 may house various illuminators for illuminating the front and back of biological growth medium 124 during imaging. The illuminators can illuminate biological growth medium 124 with one or more colors, and one or more images of biological growth medium 124 can be generated and then analyzed to determine bacteria counts on biological growth medium 124. In particular, biological reader 121 may communicate the images to computer 122, which includes a processor for performing image analysis.

Biological growth medium 124 may include a growth area 127 where bacteria or other agents manifest on biological growth medium 124. Growth area 127 may be a flat surface, a recessed well or any surface useful for biological growth.

Biological growth medium 124 may be manufactured to included nutrients in growth area 127 to facilitate the rapid growth of a particular biological agent. A sample (such as a food sample or laboratory sample) may be added to growth area along with one or more dilution agents, if desired. This process of adding a sample (and possibly a dilution agent) to growth area is referred to as inoculation, and may be performed manually by a user, or automatically by an inoculator unit (not shown in FIG. 1). Following inoculation, biological growth medium 124 may then be incubated in an incubation unit (not shown in FIG. 1). Identification element 129 may be read at the times of inoculation and incubation, and information relating to such inoculation and incubation may be recorded by computer 122 and associated with identification element 129 in order to create a detailed history of biological growth medium 124.

Following inoculation and incubation, biological growth medium 124 is processed by biological reader 121 in order to determine whether the sample being tested on biological growth medium 124 is acceptable. Identification element reader 110 may read identification element 129, and biological growth medium 124 may be inserted into biological reader 121. Computer 122 may identify manufacturing information associated with biological growth medium 124 based on identification element 129, wherein the manufacturing information includes one or more manufacturing variables measured from biological growth medium 124 when biological growth medium 124 was manufactured. Furthermore, computer 122 may adjust one or more processing parameters associated with processing of the biological growth medium 124 based on the manufacturing variables measured from the biological growth medium 124 when the biological growth medium 124 was manufactured. In the example of FIG. 1, computer 122 may adjust one or more processing parameters of biological reader 121. In this way, any manufacturing variables specific to biological growth medium 124 may be accounted for in biological reader 121, e.g., to improve the imaging process.

Alternatively, computer 122 may adjust one or more image analysis parameters based on the manufacturing variables measured from the biological growth medium 124, which may be linked to identification element 129. For example, spectroscopy measurements associated with biological growth medium 124 at the time of manufacture may be used to normalize the expected color values associated with the background color in images analyzed by computer 122. These types of normalization adjustments may be useful to account for manufacturing differences between different biological growth media, which may be due to components of such biological growth media being provided by different suppliers to the manufacturer. The normalization adjustments may comprise application of color offsets to the colors of images analyzed by computer 122 in order to account for color variations from expected colors identified by the spectroscopy measurements associated with biological growth medium 124 at the time of manufacture.

In still other cases, manufacturing information associated with biological growth medium 124 could be used to select inoculation methods or variations thereof. Also, manufacturing information associated with biological growth medium 124 could be used to direct a dwell time for gelling of biological growth medium 124. In addition, manufacturing information associated with biological growth medium 124 could be used to select or define incubation techniques or time periods for incubation. These or other processing parameters of the system could be adjusted based on the manufacturing information. Manufacturing information may also be used to define or determine how biological growth medium 124 is transported or otherwise handled at any stage of the manufacturing supply chain or at any stage of use of biological growth medium 124 in an automated system.

A determination of whether a given sample being tested in biological growth medium 124 is acceptable, in terms of bacterial colony counts or other biological agents may depend on the number of bacterial colonies per unit area. Accordingly, images generated by biological reader 121 can be analyzed by computer 122 and used to quantify the amount of bacterial colonies per unit area on biological growth medium 124. The size of individual colonies may also be factored into the analysis, if desired. Again, the surface of biological growth medium 124 in growth area 127 may contain one or more growth enhancing agents designed to facilitate the rapid growth of one or more types of bacteria or other biological agents.

As noted, biological growth medium 124 includes identification element 129, such as a bar code or other type of identification marking used to identify growth medium 124. RFID tags, two-dimensional optically detectable codes, or the like, may also be used as identification element 129. Accordingly, identification element reader 110 may comprise a bar code reader, an RFID reader, or any reader capable of reading the type of identification element being used in any given implementation.

Identification element 129 may identify the manufacturing information measured from the biological growth medium 124 when the biological growth medium 124 was manufactured. In some cases, this information may be coded into identification element, but preferably, identification element 129 is mapped to a database of information stored by computer 122. The database may include the manufacturing information measured from the biological growth medium 124 when the biological growth medium 124 was manufactured.

If desired, the database associated with computer 122 may be accessible to users or technicians via the Internet or a proprietary network. The database may be regularly updated as new biological growth media are developed or manufactured. In this way, periodic updates to the database associated with computer 122 may allow the supply chain and shelf life of different biological growth media to be recorded and tracked.

The manufacturing variables or characteristics measured from biological growth medium 124, and associated with identification element 129 may comprise one or more spectroscopy measurements measured from the biological growth medium when the biological growth medium was manufactured, such as spectroscopy absorption measurements and/or spectroscopy transmission measurements. Again, these types of spectroscopy measurements may be used to tune or adjust biological reader 121, e.g., by adjusting the illumination sources, illumination angles, or camera exposures used for generating images of biological growth medium 124, or by adjusting algorithms used by computer 122 to count biological agents from such images.

As yet another example, the manufacturing variables measured from biological growth medium 124, and associated with identification element 129 may comprise measurements of background color of biological growth medium 124 at the time of manufacture. These types of measurements may also be used to tune or adjust biological reader 121, e.g., by adjusting the illumination sources, illumination angles, or camera exposures used when generating images of biological growth medium 124, or by adjusting algorithms used by computer 122 to count biological agents from such images.

Other types of manufacturing information that may be measured from biological growth medium 124, and associated with identification element 129 may comprise information such as a plate type associated with biological growth medium 124, a manufacturing date associated with biological growth medium 124, a manufacturing lot code associated with biological growth medium 124, a manufacturing lot expiration date associated with biological growth medium 124, and/or a manufacturer of biological growth medium 124. This information may also be used during the processing of biological growth medium 124, e.g., providing the ability to check for quality control and media authentication, and may supplement the manufacturing information that is measured from biological growth medium 124 when biological growth medium 124 was manufactured. As an example, the date of manufacture could be read in order to facilitate adjustments to one or more aspects of the biological growth media processing system, e.g., to compensate for shelf life or aging artifacts of biological growth medium 124.

In addition to manufacturing information, other information may also be recorded and associated with identification element 129. For example, sample information related to a sample being tested by biological growth medium 124 may be recorded and associated with identification element 129. In addition, service information about biological growth medium processing system 120 may also be recorded and associated with identification element 129.

In these cases, identification element 129 of the biological growth medium may be linked to manufacturing information associated with the biological growth medium 124, sample information related to a sample being tested on biological growth medium 124, and service information about biological growth medium processing system 120.

As examples, the sample information may include a type of sample being tested on biological growth medium 124, information about a dilution agent used with the sample, and/or an origin associated with the sample being tested on the biological growth medium. These types of information may be linked to biological growth medium 124 when the sample is inoculated on growth area 127. Also, sample information may include an incubation time, e.g., a duration associated with incubation of a particular sample tested on biological growth medium 124. This type of information may be linked to biological growth medium 124 when biological growth medium 124 is incubated. In some cases, at least some of the sample information may be recorded when the count value is generated by computer 122. This type of sample information generated by computer 122 may include such things as a date that the count value is generated, and a technician associated with the processing.

The service information may comprise information about biological growth medium processing system 120, which may be defined and used by service technicians in order to service the system. As examples, the service information may comprise counting rules applied by biological growth medium processing system 120. e.g., counting rules applied by either biological reader 121 or by computer 122, a temperature associated with incubation of biological growth medium 124 in an incubator (not shown) of biological growth medium processing system 120, a difference between an automated count value generated by biological reader 121 or computer 122 and a human count, information indicative of human intervention with biological growth medium processing system 120 during the processing of biological growth medium 124, ambient conditions in proximity to biological reader 121 when images are generated, throughput statistics associated with biological growth medium processing system 120, data or other information related to control samples or control tests, or other service-type information that may be useful to a service technician.

The service-type information could be gathered in order to monitor usage of biological growth medium processing system 120 and to anticipate times that system 120 should be serviced. Biological growth medium processing system 120 may be configured to prompt users to order more biological growth media based on service-type usage information stored in the database. Service-type information may also be useful in rental arrangements in which the user rents one or more components of biological growth medium processing system 120. In addition, service-type information may allow service technicians to study customer usage of biological growth medium processing system 120 in order to facilitate automation enhancements and future developments and improvements to system 120.

After biological growth medium 124 is processed in biological growth medium processing system 120, a user may read identification element 129 of biological growth medium 124 another time using identification element reader 110. At this point, identification element 129 may identify the manufacturing information, the sample information, the service information and the count value. Identification element reader 110 may access a database of computer 122 in order to determine the manufacturing information, the sample information, the service information and the count value associated with identification element 129. Times associated with the various processing steps may also be recorded and associated with identification element 129. In this way, following processing of biological growth medium 124, a full set of useful information may be accessible for analysis or use by various persons.

As one example, biological growth medium 124 may comprise a biological growth plate sold by 3M under the trade name PETRIFILM plates. Biological growth medium 124 can be utilized to facilitate the rapid growth and detection of bacteria or other biological agents commonly associated with food contamination, including, for example, aerobic bacteria, *E. coli*, coliform, *Enterobacteriaceae* species, yeast, mold, *Staphylococcus aureus, Listeria* species, *Campylobacter* species, or the like. Growth plates are generally one type of growth medium commonly used for biological growth and bacterial detection and enumeration. The invention, however, may also be applied with a wide variety of other types of growth media, such as agar, broth, or media-coated sensors.

Figure 2A:
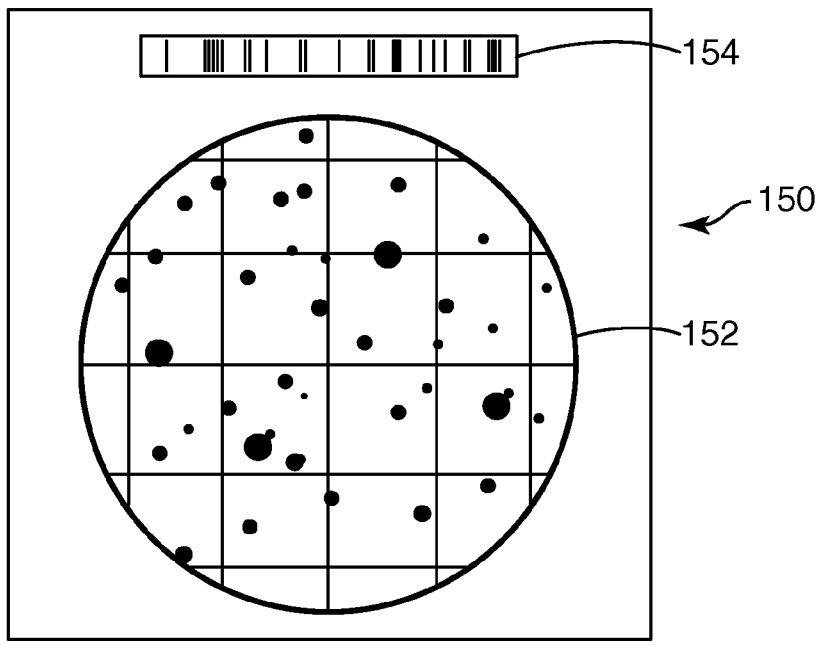
FIGS. 2A and 2B are top views of exemplary biological growth media in the form of biological growth plates according to this disclosure.
Figure 2B:
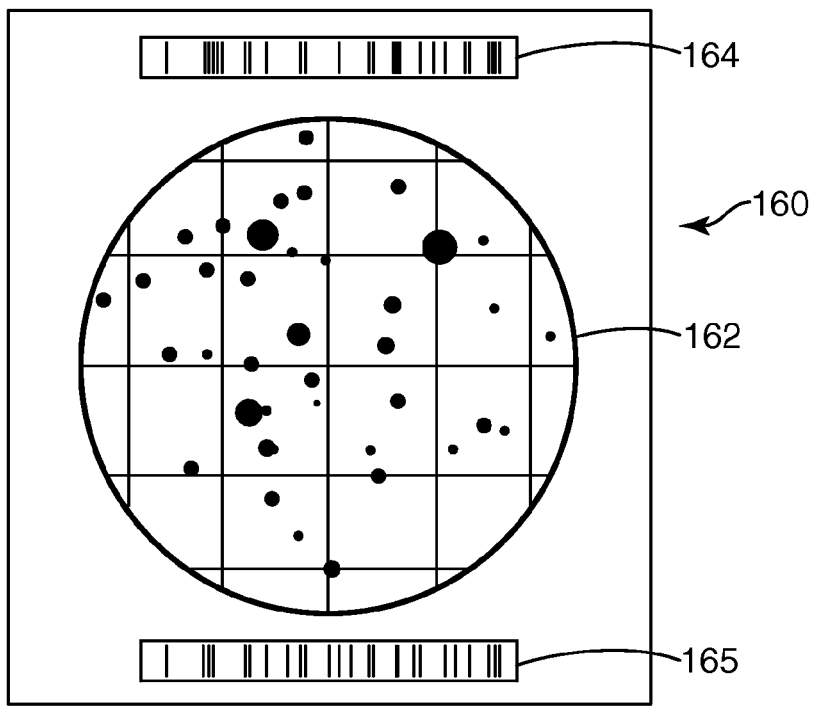

FIGS. 2A and 2B are top views of an exemplary biological growth media in the form of biological growth plates 150 and 160. By way of example, biological growth plates 150, 160 may comprise biological growth plates sold by 3M under the trade name PETRIFILM plates. In accordance with this disclosure, biological growth plate 150 includes identification element 154 to facilitate information management techniques discussed herein. Identification element 154 of the biological growth plate 150 may be linked to manufacturing information associated with the biological growth medium, such as manufacturing information measured from the biological growth plate 150 when biological growth plate 150 was manufactured. In addition, identification element 154 of the biological growth plate 150 may be linked to sample information related to a sample being tested biological growth plate 150, and/or service information about a biological growth medium processing system used to process biological growth plate 150.

Biological growth plate 160 includes first identification element 164 and second identification element 165 to facilitate information management techniques discussed herein. The illustrated locations of elements 164 and 165 are exemplary, and elements 164, 165 could be located in other locations on biological growth plate 160. First identification element 164 of the biological growth plate 160 may be linked to manufacturing information associated with the biological growth medium, such as manufacturing information measured from the biological growth plate 160 when biological growth plate 160 was manufactured. First identification element 164 may be added to biological growth plate 160 at the time of manufacture.

Second identification element 165 of the biological growth plate 160 may be added to biological growth plate 160 during the processing of biological growth plate 160, such as when a sample is added to growth area 162 during inoculation. Second identification element 165 may be linked to sample information related to a sample being tested biological growth plate 160, and/or service information about a biological growth medium processing system used to process biological growth plate 160. If desired, a third identification element (not shown) could be used such that manufacturing information is linked to first identification element 164, sample information is linked to second identification element 165, and service information is linked to third identification element (not shown). In some cases, second identification element 165 may include a machine-readable zone and a human readable zone for labeling purposes.

In the examples of FIGS. 2A and 2B, identification elements 154, 164 and 165 are illustrated as optically readable patterns, e.g., bar codes. In other cases, however, identification elements 154, 164 and 165 may assume a wide variety of optical patterns such as characters, bar codes, two-dimensional bar codes, optical gratings, holograms, phosphorous inks and the like. Moreover, in some embodiments, identification elements 154, 164 and 165 comprise visible or non-visible circuits or magnetic elements, which may be readable by magnetic or radio frequency techniques. For example, one or more of identification elements 154, 164 and 165 may comprise any of a wide variety of radio frequency identification (RFID) tags commonly used in many industries for inventory tracking purposes. If human-readable characters are used for one or more of identification elements 154, 164 and 165, optical character recognition techniques may be used to facilitate automated reading of such characters.

Biological growth plates 150, 160 may facilitate the rapid growth and detection and enumeration of bacteria or other biological agents including, for example, aerobic bacteria, *E. coli*, coliforms, *Enterobacteriaceae* species, yeast, mold, *Staphylococcus aureus, Listeria* species, and *Campylobacter* species, and the like. The use of PETRIFILM plates, or other growth media, can simplify bacterial testing of food samples. Moreover, as outlined herein, a biological growth medium processing system can further simplify such testing by providing automated handling, analysis an information tracking of such media.

As shown in FIGS. 2A and 2B, biological growth plates 150, 160 each define a growth area 152, 162. A determination of whether a given sample being tested in biological growth plate 150, 160 is acceptable, in terms of bacterial colony counts, may depend on the number of bacterial colonies per unit area. Accordingly, the biological growth medium processing system may quantify the amount of bacterial colonies per unit area on biological growth plates 150, 160, and may compare the amount, or "count," to a threshold. The surface of biological growth plates 150, 160 may contain one or more growth enhancing agents designed to facilitate the rapid growth of one or more types of bacteria or other biological agents.

Inoculation refers to the process of adding a sample of material being tested to the surface of biological growth plate 150 or 160 within growth area 152 or 162. After inoculation, biological growth plate 150 or 160 can be inserted into an incubation chamber (not shown). In the incubation chamber, bacterial colonies or other biological agents being grown by biological growth plate 150 or 160 manifest themselves, as shown in biological growth plates 150 and 160 of FIGS. 2A and 2B. The colonies, represented by various dots on biological growth plates 150 and 160 of FIGS. 2A and 2B, may appear in different colors relative to the background colors of growth areas 152 and 162, facilitating automated detection and enumeration of bacterial colonies via image analysis techniques.

As described in this disclosure, the colors that are associated with the background of growth areas 152 and 162, as well as the colors associated with the biological agents that are grown in growth areas 152 and 162 may be affected by manufacturing variables. The components used to manufacture biological growth plates 150, 160, such as a top cover that overlays growth areas 152 and 162, for example, may affect the expected colors that manifest on biological growth plates 150, 160. By measuring variables at the time of manufacture, such as spectroscopy transmission or absorption associated with the top covers of biological growth plates 150, 160, automated image analysis via a computer may be normalized to account for manufacturing variations and differences. In this way, by linking identification elements 154, 164 to measured manufacturing variables, an automated system can be programmed to address and normalize for such manufacturing variations and differences.

Figure 3:
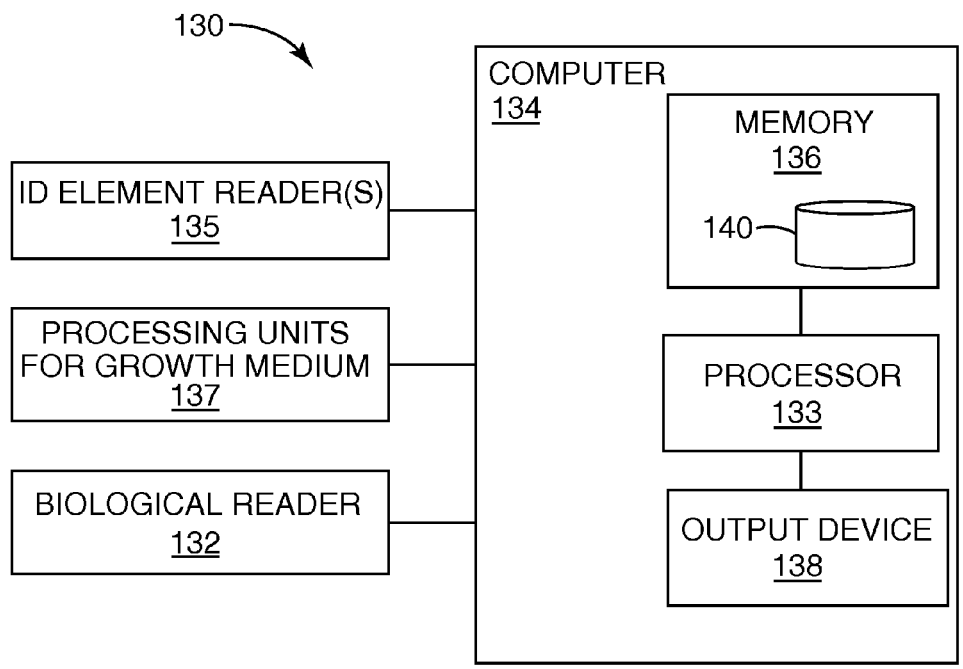
FIG. 3 is a block diagram of a biological growth medium processing system consistent with this disclosure.

FIG. 3 is a block diagram of a biological growth medium processing system 130, which may correspond to biological growth medium processing system 120 of FIG. 1 or another system, such as a modular system discussed in greater detail below. Biological growth medium processing system 130 includes a computer 134, which may include a processor 133 coupled to memory 136. If desired, computer 134 may also be coupled to an output device 138, such as a display screen. Computer 134 is coupled to one or more identification (ID) element readers 135, and one or more processing units 137. An example of a processing unit is biological reader 132, which is coupled to computer 134 and illustrated separately in FIG. 3.

Biological reader 132 includes an imaging device that generates one or more images of a biological growth medium and provides the images to computer 134. Computer 134 includes a processor 133 coupled to memory 136. Memory 136 stores various processor-executable software instructions that facilitate image analysis of the images generated by biological reader 132, and processor executes such instructions. In particular, memory 136 stores one or more counting algorithms or rules that can be applied by processor 133 during image analysis in order to improve the accuracy of automated counts of biological agents on a biological growth plate, e.g., relative to manual counting by a person. Output device 138 receives the results determined by processor 133 and provides the results to a user.

Figure 4:
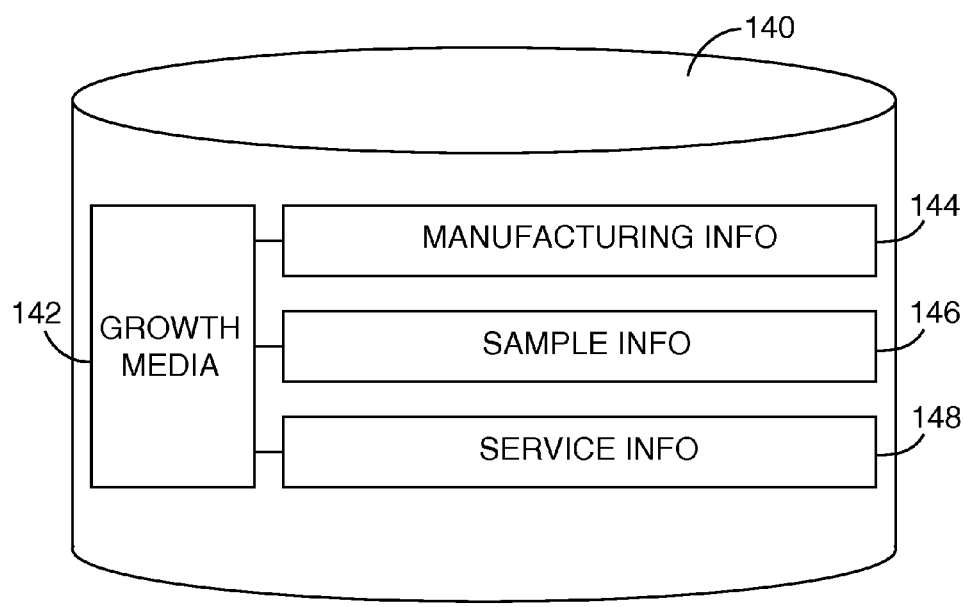
FIG. 4 is a more detailed illustration of a database of a computer in the biological growth medium processing system shown in FIG. 3.

According to this disclosure, memory 136 also stores a database 140, and may store database management software for the management of database 140. A more detailed illustration of database 140 is shown in FIG. 4. Processor 133 may executed database management software programmed to create the database structures described in this disclosure. Database 140 of memory 136 can be used to associate the different types of information described herein with different biological growth media.

For example, as illustrated in FIG. 4, database 140 may associate different biological growth media 142 to manufacturing information 144, sample information 146 and/or service information 148. Identification elements of the biological growth media may be read by identification element reader 135 and communicated to computer 134. Processor 133 may access, store, record, assemble, and/or associate the different types of information 144, 146 and 148, respectively, with each of the different biological growth media 142 based on ID values of the identification elements. In this way, database 140 of computer 134 facilitates information tracking of biological growth media 142. The different types of information 144, 146 and 148 may be defined at different times over the course of manufacturing and processing of biological growth media 142.

Manufacturing information 144 may define one or more manufacturing variables measured for biological growth media 142. In this case, processor 133 of computer 134 may adjust one or more parameters of an image analysis process based on manufacturing information 144 of the different biological growth media 142 in order to account for manufacturing variations between different biological growth media 142. For example, spectroscopy measurements associated with different biological growth media 142 at the time of manufacture may be used to normalize the expected color values associated with the background color or the colors of biological agents in images generated by biological reader 132 and analyzed by computer 134. Such normalization adjustments to colors in the images generated by biological reader 132 and analyzed by computer 134 may be useful to account for manufacturing differences between different biological growth media 142, which may be due to components of such biological growth media being provided by different suppliers. In this case, computer 134 may apply offset values to the colors in images of the biological growth media in order to normalize and account for measured manufacturing differences between different biological growth media.

In addition to the measured manufacturing variables, manufacturing information 144 may also include information such as plate types associated with biological growth media 142, manufacturing dates associated with biological growth media 142, manufacturing lot codes associated with the biological growth media 142, and the manufacturer(s) of biological growth media 142. This information may also be used during the processing of the biological growth media 142, and may supplement the manufacturing information that is measured from biological growth media 142 when biological growth media 142 were manufactured.

Such manufacturing information may also be used to authenticate a biological growth medium as being provided by a known and reliable company, which can help to ensure quality control during biological testing. For example, one or more manufacturers may be specifically validated, e.g., on the basis of production quality and performance criteria of the biological growth media. In some cases, biological reader 132 may be configured to reject biological growth media that are not validated via identification elements as being associated with validated manufacturers. This type of authentication can provide security and prevent fraudulent introduction of unauthorized growth plates, e.g., to thwart the food inspection or laboratory analysis process.

In one example, manufacturing information 144 may include first information indicative of a plate type associated with the biological growth medium, second information indicative of a manufacturer of the biological growth medium, and third information that includes the one or more manufacturing variables measured from the biological growth medium when the biological growth medium was manufactured. Computer 134 may select an image processing profile to be used by biological reader 132 for the biological growth medium based on the first information, verify the manufacturer of the biological growth medium based on the second information, and adjust parameters of biological reader 132 based on the third information. Biological reader 132 may generate one or more images of the biological growth medium based on the adjusted parameters, and computer 134 may process the one or more images based on the selected imaging processing profile.

Manufacturing information 144 may further include fourth information indicative of a manufacturing date associated with the biological growth medium. In this case, computer 134 may determine an expiration date associated with the biological growth medium based on the manufacturing date, and identify the biological growth medium as expired if the expiration date has passed. In some embodiments, the detection of expired biological growth medium could cause the system to generate a caution message to have the sample re-tested. Alternatively, computer 134 may determine an expiration date associated with the biological growth medium based on the manufacturing date, and adjust one or more of the processing parameters associated with the processing of the biological growth medium based on the expiration date. In some cases, manufacturing information 144 may also include fifth information indicative of a manufacturing lot code associated with the biological growth medium, and possibly other manufacturing information.

In addition to manufacturing information 144, database 140 also stores sample information 146 related to samples being tested by biological growth media 142. In this case, the identification elements of the biological growth media 142 may be linked to manufacturing information 144, and to sample information 146 related to samples being tested on different biological growth media 142.

As examples, sample information 146 may include the types of samples being tested on biological growth media 142, information about dilution agents used with different samples during inoculation, and/or origins associated with samples being tested on biological growth media 142. Also, sample information 146 may include an amount of time associated with incubation of biological growth media 142. In some cases, at least some of sample information 146 may be recorded when the count values are generated by computer 134 based on the analysis of images generated by biological reader 132 for biological growth media 142. This type of recorded sample information may include such things as date that the count values are generated, and technicians associated with the processing.

Furthermore, in addition to manufacturing information 144 and sample information 146, database 140 may also store service information 148 and associate service information 148 with biological growth media 142. Service information 148 may comprise information about biological growth medium processing system 130, which may be defined and used by service technicians in order to service system 130. As examples, the service information may comprise counting rules applied by processor 133 of computer 134 in the analysis of images generated by biological reader 132 for biological growth media 142, temperatures associated with incubation of biological growth media 142 in an incubator of biological growth medium processing system 130 (which may comprise one of processing units 137), a difference between count values generated by computer 134 and manual human counts, information indicative of human intervention with biological growth medium processing system 130 during the processing of biological growth media 142, ambient conditions in proximity to biological reader 132 when images are generated, or other service-type information that may be useful to a service technician.

FIGS. 5A and 5B are perspective illustrations of one exemplary embodiment of a modular processing system 10 capable of implementing one or more of the techniques described in this disclosure. FIG. 5A is an exploded perspective view, and FIG. 5B is an assembled perspective view. As illustrated, modular processing system 10 comprises an automated loading module 12, a modular incubator 14, a second automated loading module 16, an automated reader 18, and a collator 20. Interlocking features 30 facilitate proper interlocking attachment of automated loading module 12, modular incubator 14, second automated loading module 16, automated reader 18, and collator 20. Automated loading module 12, modular incubator 14, second automated loading module 16, automated reader 18, and collator 20 each include input slots 26 for receiving a biological growth medium 22 that includes a growth area 23 designed for rapid growth of biological agents.

Biological growth medium 22 may include an identification element 25 as described herein. Identification element 25 may comprise a bar code, RFID tag, or any element or indicia capable of identifying biological growth medium 22. Information is associated with biological growth medium 22 via identification element 25.

In particular, identification element 25 may be used to associate manufacturing information, sample information and service information with biological growth medium 22. The manufacturing information may be defined for biological growth medium 22 and associated with identification element 25 when biological growth medium 22 is manufactured. Again, this manufacturing information may include measured characteristics of biological growth medium 22, and possibly other manufacturing variables or characteristics.

The sample information may be recorded and associated with biological growth medium 22 when a sample is added to growth area 23, e.g., in an inoculation process. The sample information comprises information related to the specific sample being tested on biological growth medium 22. The inoculation process may be performed manually by a user, or could be automated into a modular inoculation unit (not shown).

The service information may be recorded and associated biological growth medium 22 as medium 22 is processed through modular processing system 10. The service information comprises information about modular processing system 10, which may be used by a service technician to diagnose problems and to provide service to system 10.

In practice, growth area 23 of biological growth medium 22 is inoculated with a sample, and biological growth medium is inserted into automated loading module 12, which is illustrated as including a stack 24 of biological growth media. Automated loading module 12 is aligned with modular incubator 14 and loads biological growth media into modular incubator 14 for incubation. Following incubation, the biological growth media are ejected from modular incubator 14 into second automated loading module 16. The biological growth media are then inserted into automated reader 18, which captures images of the biological growth media. After automated reader 18 captures the images, the biological growth media are ejected from automated reader 18 into collator 20, where the processed biological growth media are staked and collected.

The illustrated modules of FIGS. 5A and 5B are exemplary processing modules. Other types of processing modules could also be used. One or more of the different modules of FIGS. 5A and 5B may include identification element readers to read identification element 25 of biological growth medium 22, as biological growth medium 22 is processed through modular processing system 10. Some or all of the processing modules shown in FIGS. 5A and 5B may be coupled to a computer, which may process data associated with biological growth medium 22.

Figure 6:
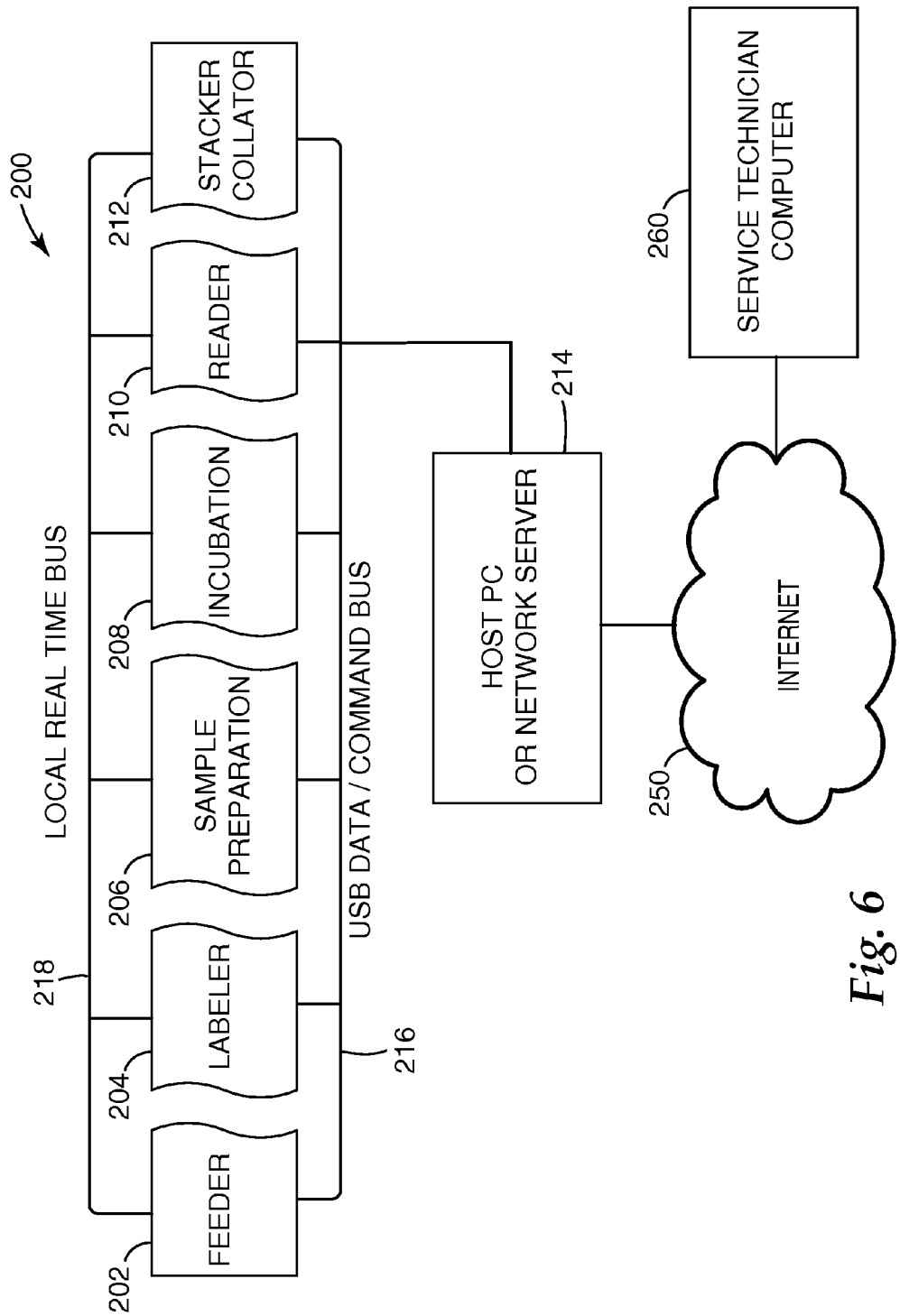
FIG. 6 is a block diagram of an exemplary system capable of implementing one or more of the techniques described in this disclosure.

FIG. 6 is a block diagram of an exemplary system 200 comprising automated feeder module 202, labeler 204, sample preparation module 206, incubation module 208, reader module 210, and stacker collator 212. Feeder module 202 may function as described above in reference to automated loading module 12 of FIGS. 5A and 5B. Similarly, incubation module 208 may function as described above in reference to modular incubator 14. In addition, reader module 210 may function as described above in reference to automated reader 18, and stacker collator 212 may function as described above in reference to collator 20.

Feeder module 202 includes biological growth media that include identification elements. The identification elements of the biological growth media identify manufacturing information associated with the biological growth media. For example, the identification elements may store the manufacturing information or may store pointers to manufacturing information, e.g., stored in a database of computer 214.

Labeler 204 may be used to label identification elements on the biological growth media. For example, FIG. 2B illustrates a biological growth plate 160 that includes first identification element 164 and second identification element 165. As noted, first identification element 164 may be added at the time of manufacture of biological growth plate 160 and may be linked to variables or characteristics measured from biological growth plate 160 at the time of manufacture. Second identification element 165 may be added during the processing of biological growth plate 160, and may be linked to sample information and/or service information. Labeler 204 of FIG. 6 may be used to label second identification element 165 on biological growth plate 160. Some of all of the modules shown in FIG. 6 may include identification element readers to facilitate automated tracking and collection of information associated with the biological growth medium. The identification element readers may comprise bar code scanners, RFID readers, or another type of reader if another type of identification element is used on the biological growth media.

Sample preparation module 206 may comprise an inoculation device that inoculates a biological growth medium with samples. Sample preparation module 206 may also perform other functions, such as adding dilution agents to the biological growth medium. Sample information and possibly service information may be recorded at this time and linked to the identification element of the biological growth medium. In this case, sample information may include a type of sample being tested, information about a dilution agent used with the sample, or an origin associated with the sample being tested, and service information may comprise information about the sample preparation module 206, such as conditions or temperatures associated with sample preparation module 206, or information indicative of human intervention with sample preparation module 206.

Incubation unit 208 incubates the biological growth medium to rapidly grow biological agents that may be present in the sample. Sample information and possibly service information may be recorded at this time and linked to the identification element of the biological growth medium. For example, the incubation time may be recorded as sample information, and incubation conditions or temperatures associated with incubation unit 208 may be recorded as service information. In addition, service information may include information indicative of human intervention with incubation unit 208. The incubation time comprising a duration that an inoculated biological growth medium is incubated in incubation unit 208 may also be recorded as service information. The incubation time may be recorded in automated fashion, e.g., by reading the identification element associated with the biological growth medium when it is received and when it is ejected from incubation unit 208, which can ensure a reliable automated determination of the duration associated with incubation.

Following incubation, reader module 210 generates one or more images of the biological growth medium and provides such images to computer 214 for image analysis. Sample information and possibly service information may also be recorded at this time and linked to the identification element of the biological growth medium. In this case, sample information may include a date and possibly a time that the count value is generated, and possibly a technician associated with the processing. The service information may comprise counting rules applied by computer 214, conditions or parameters associated with reader module 210, a difference between the count value and a human count, information indicative of human intervention with reader module 210, and/or ambient conditions in proximity to reader module 210 when images of the biological growth medium are generated.

Stacker collator 212 collects processed biological growth media, and stacks the biological growth media. The biological growth media may then be removed, stored, or possibly discarded. Sample information and possibly service information may also be recorded at this time and linked to the identification element of the biological growth medium. In this case, sample information may include a date and possibly a time of the stacking, and the service information may comprise as conditions or temperatures associated with stacker collator 212 or information indicative of human intervention with stacker collator 212.

Some or all of modules 202, 204, 206, 208, 210 and 212 may be connected via a local bus 218 in order to properly advance a biological growth medium through system 200. For example, local bus 218 may arbitrate time critical events such as intermodule transport of the biological growth media.

In addition, some or all of modules 202, 204, 206, 208, 210 and 212 may be coupled to a computer 214 via a data/command bus 216. As examples, data/command bus 216 may comprise a Universal Serial Bus (USB) connection, a Universal Serial Bus 2 (USB2) connection, an IEEE 1394 FireWire connection, a Small Computer System Interface (SCSI) connection, an Advance Technology Attachment (ATA) connection, a serial ATA connection, a Peripheral Component Interconnect (PCI) connection, a conventional serial or parallel interface connection, or the like.

Computer 214, in turn may be coupled to the Internet 250, or possibly anther public or private network. A service technician computer 260 may be communicatively coupled to computer 214 via the Internet 250. Accordingly, a service technician may have access to the service information collected about system 200 during the processing of different biological growth media. This can facilitate improved service by the technician. Moreover, since service information is stored separately from the sample information, the service information may be transparent to users that are most interested in the sample information. Instead, the service information may be accessed by a technician if any problems arise in system 200.

In accordance with this disclosure, the manufacturing information associated with a biological growth medium may be identified, and then used by one or more of modules 202, 204, 206, 208, 210 and 212 during the processing of that biological growth medium. As noted, one or more of modules 202, 204, 206, 208, 210 and 212 may include an identification element reader. Upon reading an identification element, data associated with that identification element may be obtained from a database in computer 214.

System 200 may configure or adjust one or more processing parameters for the processing of different biological growth media based on manufacturing variables or parameters measured from the different biological growth media, which may be linked to the identification elements of the different biological growth media. In this way, variables specific to different biological growth media can be used to adjust such things as sample preparation by sample preparation module 206, incubation by incubation module 208, image generation by reader module 210, or image analysis by computer 214.

Furthermore, sample information and possibly service information may be defined and recorded by system 200 for each specific biological growth medium as the biological growth medium is processed in system 200. Then, any subsequent readout of the identification element of a given biological growth medium can be used to find the manufacturing information, the sample information and the service information recorded over the life cycle of that biological growth medium.

Moreover, in addition to tracking the different types of information associated with the biological growth media, this disclosure also contemplates time tracking of the various processing stages of a given biological growth medium. For example, any time an image is generated by reader module 210 for a given biological growth medium, the timing associated with this image may be recorded and associated with that image. Furthermore, the timing of sample preparation (inoculation) via sample preparation module 206, and incubation via incubation module 208 may be recorded and associated with the biological growth medium via its identification element. In this way, the techniques of this disclosure can record and preserve a time history associated with each processing stage of the biological growth medium. As an example, computer 214 may record times associated with inoculating, incubating and generating the one or more images of a biological growth medium, and associate the times with an identification element of the biological growth medium to create a processing history associated with the biological growth medium.

Figure 7:
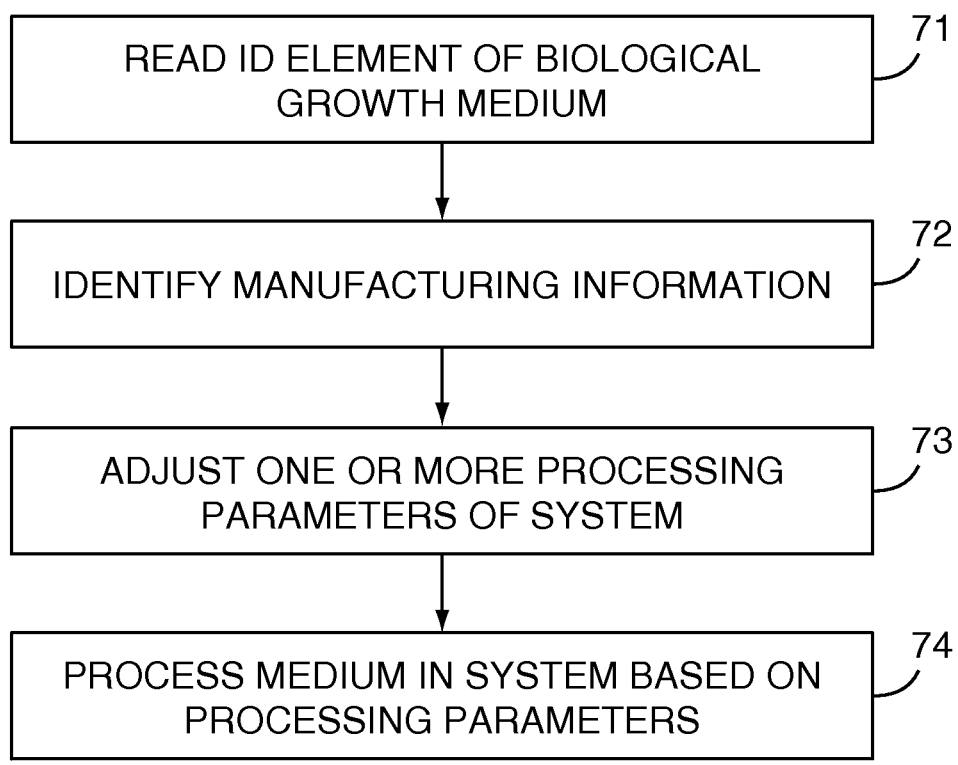
FIGS. 7-9 are flow diagrams illustrating techniques of this disclosure.

FIG. 7 is a flow diagram illustrating a technique that may be performed by a biological growth medium processing system. FIG. 7 will be described from the perspective of biological growth medium processing system 120 of FIG. 1. The technique of FIG. 7, however, could also be performed by a modular system such as that shown in FIGS. 5A, 5B and 6, or in another system. Referring to step 71 in FIG. 7, identification element reader 110 reads an identification element 129 of biological growth medium 124. Based on the readout of identification element 129 computer 122 identifies manufacturing information associated with biological growth medium 124 in step 72, which includes information measured from biological growth medium 124 when biological growth medium 124 was manufactured. In step 73, computer 122 adjusts one or more processing parameters of biological growth medium processing system 120 based on the identified manufacturing information. In step 74, biological growth medium 124 is then processed in biological growth medium processing system 120 based on the adjusted processing parameters.

As explained in detail above, the manufacturing information measured from biological growth medium 124 may comprise one or more spectroscopy measurements measured when the biological growth medium 124 was manufactured, such as spectroscopy absorption measurements and/or spectroscopy transmission measurements. These types of spectroscopy measurements may be used to tune or adjust biological reader 121, e.g., by adjusting the illumination sources, illumination angles, or camera exposures used for generating images of the biological growth medium 124, or by adjusting algorithms used by computer 122 to count biological agents from such images. For example, spectroscopy measurements associated with biological growth medium 124 at the time of manufacture may be used to normalize the expected color values associated with the background color or other colors rendered on of biological growth medium. In this case, the spectroscopy measurements may be applied by computer 122 that analyzes images produced by a biological reader, e.g., by applying offset values, in order to normalize the expected color values.

As yet another example, the manufacturing information measured from the biological growth medium 124 when the biological growth medium was manufactured may comprise direct measurements of background color of the biological growth medium 124. These types of measurements may also be used to tune or adjust biological reader 121, or by adjusting or normalizing expected color values associated with images analyzed by computer 122 in counting biological agents from such images.

Figure 8:
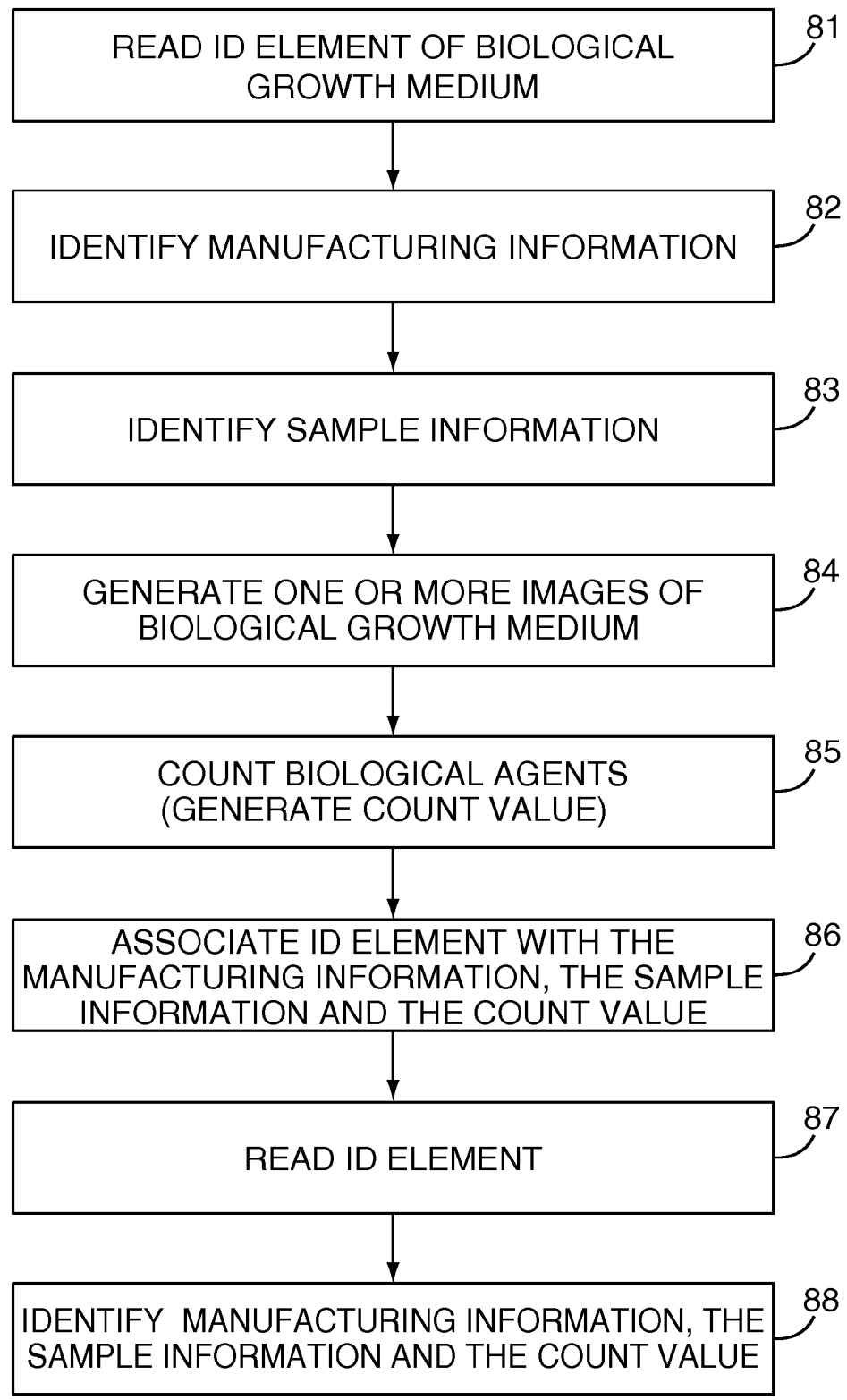

FIG. 8 is another flow diagram illustrating a technique that may be performed by a biological growth medium processing system. FIG. 8 will also be described from the perspective of biological growth medium processing system 120 of FIG. 1, although the technique of FIG. 8 could also be performed by a modular system such as that shown in FIGS. 5A, 5B and 6, or in another system.

Referring to step 81 in FIG. 8, identification element reader 110 reads an identification element 129 of biological growth medium 124. Based on the readout of identification element 129, computer 122 identifies manufacturing information associated with biological growth medium 124 in step 82, and, in step 83, identifies sample information associated with a sample being tested on biological growth medium 124. In step 84, biological growth medium 124 is then received by biological reader 121, which generates one or more images of biological growth medium 124. Such images are communicated to computer 122, which uses the one or more images to count biological agents on biological growth medium 124 based on the images in step 85. In doing so, computer 122 generates a count value.

In step 86, computer 122 then associates the identification element of biological growth medium 124 with the manufacturing information, the sample information and the count value, e.g., in a database of computer 122. Then, if identification element reader 110 reads identification element 129 of biological growth medium 124 a second time (e.g., as in step 87), computer 122 can identify the manufacturing information, the sample information and the count value (e.g., as in step 88). In this way, computer 122 assembles information desirable for biological growth medium 124, and can provide such information to a user based on readout of identification element 129 by identification element reader 110.

Figure 9:
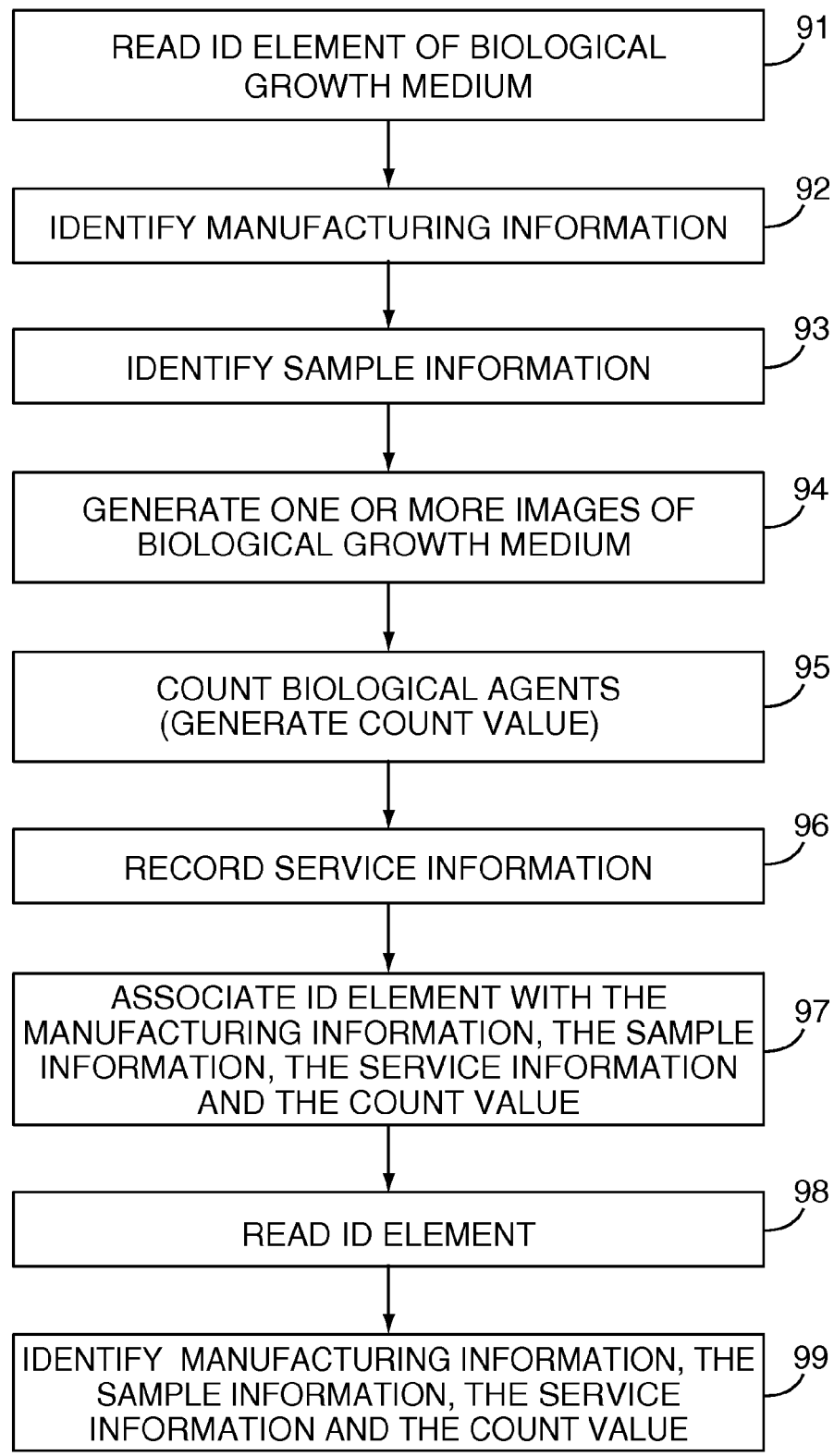

FIG. 9 is another flow diagram illustrating a technique that may be performed by a biological growth medium processing system. FIG. 9 will also be described from the perspective of biological growth medium processing system 120 of FIG. 1, although the technique of FIG. 9 could also be performed by a modular system such as that shown in FIGS. 5A, 5B and 6, or in another system.

Referring to step 91 in FIG. 9, identification element reader 110 reads an identification element 129 of biological growth medium 124. Based on the readout of identification element 129 computer 122 identifies manufacturing information associated with biological growth medium 124 in step 92, and, in step 93, identifies sample information associated with a sample being tested on biological growth medium 124. In step 94, biological growth medium 124 is then received by biological reader 121, which generates one or more images of biological growth medium 124. Such images are communicated to computer 122, which uses the one or more images to count biological agents on biological growth medium 124 based on the images in step 95. In doing so, computer 122 generates a count value.

During this processing of biological growth medium 124 in step 96, computer 122 records service information. As described in this disclosure, the service information comprises information about biological growth medium processing system 120, such as information about biological reader 121. For example, the service information may comprise one or more of counting rules applied by computer 122 of biological growth medium processing system 120, a temperature associated with incubation of the biological medium in an incubator (not shown in FIG. 1), a difference between the count value and a human count, any information indicative of human intervention with the biological growth medium processing system 120 during the processing of biological growth medium 124, ambient conditions in proximity to biological reader 121 when images of the biological growth medium 124 are generated, or throughput statistics of biological growth medium processing system 120, such as a number of media and types of media processed through system 120.

Referring to step 97 in FIG. 9, computer 122 then associates the identification element of biological growth medium 124 with the manufacturing information, the sample information, the service information and the count value, e.g., in a database of computer 122. Then, if identification element reader 110 reads identification element 129 of biological growth medium 124 a second time (e.g., as in step 98), computer 122 can identify the manufacturing information, the sample information, the service information, and the count value (as shown in step 99). In this way, computer 122 assembles information desirable for biological growth medium 124, and can provide such information to a user based on readout of identification element 129 by identification element reader 110. Also, a technician may be able to access service information based on identification element 129 of biological growth medium 124, in order to obtain insight into service that may be needed for biological growth medium processing system 120.

The techniques described herein may be implemented in hardware, software, firmware, or any combination thereof. If implemented in software, the techniques may be realized at least in part by a computer-readable medium comprising instructions that, when executed by computer of a biological growth medium processing system cause the computer to perform one or more of the techniques of this disclosure. The computer-readable data storage medium may form part of a computer program product, which may include packaging materials. The computer-readable medium may comprise random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like.

The computer-readable instructions may be executed in the computer of the system by one or more processors, general purpose microprocessors, ASICs, FPGAs, or other equivalent integrated or discrete logic circuitry. Accordingly, the term "processor," as used herein may refer to any structure suitable for implementation of the techniques described herein.

For software embodiments, this disclosure may provide a computer-readable medium comprising instructions that upon execution in a computer of a biological growth medium processing system cause the computer to receive a reading of an identification element read from a biological growth medium identify manufacturing information associated with the biological growth medium based on the identification element, wherein the manufacturing information includes one or more manufacturing variables measured from the biological growth medium when the biological growth medium was manufactured, adjust one or more processing parameters associated with processing of the biological growth medium based on the manufacturing variables measured from the biological growth medium when the biological growth medium was manufactured, and cause the system to process the biological growth medium based on the processing parameters.

In addition, this disclosure may provide a computer-readable medium comprising instructions that upon execution in a computer of a biological growth medium processing system cause the computer to receive a reading of one or more identification elements of a biological growth medium, identify manufacturing information related to the biological growth medium based on the one or more identification elements of the biological growth medium, identify sample information related to a sample being tested by the biological growth medium based on the one or more identification elements of the biological growth medium, receive a count value, the count value comprising a quantified value associated with biological agents formed on the biological growth medium, and associate the one or more identification elements with the manufacturing information, the sample information and the count value.

If implemented in hardware, this disclosure may be directed to a circuit, such as an integrated circuit, ASIC, FPGA, logic, or various combinations thereof configured to perform one or more of the techniques described herein. Various modifications may be made without departing from the spirit and scope of the invention. These and other embodiments are within the scope of the following claims.

The invention claimed is:

1. A method comprising:
reading, by an identification element reader of a biological growth medium processing system, an identification element associated with a biological growth plate for growing and detecting bacterial colonies, wherein the biological growth plate is obtained from a particular manufacturing lot;
identifying, by a computer of the system, manufacturing information associated with the particular manufacturing lot using the identification element;
wherein the manufacturing information includes one or more spectroscopy measurements measured from the biological growth plate when the biological growth plate was manufactured;
identifying, by the computer, based on the spectroscopy measurements, variations from expected colors;
inoculating the biological growth plate;
generating, by a biological reader of the system, an image of the biological growth plate after bacterial colonies have formed on the biological growth plate;
modifying, by the computer, the image by applying color offsets to colors of the image of the biological growth plate, thereby accounting for the variations from the expected colors; and
counting, by the computer, using the modified image, the bacterial colonies on the biological growth plate.

2. The method of claim 1, wherein the one or more spectroscopy measurements comprise spectroscopy absorption measurements and spectroscopy transmission measurements.

3. The method of claim 1, wherein the manufacturing information includes:
first information indicative of a plate type associated with the biological growth plate;
second information indicative of a manufacturer of the biological growth plate; and
third information that includes the one or more manufacturing variables measured from the biological growth plate when the biological growth plate was manufactured.

4. The method of claim 3, wherein the image is a first image, the method further comprising:
selecting, by the computer, an image processing profile to be used by the biological reader for the biological growth plate using the first information;
verifying, by the computer, the manufacturer of the biological growth plate using the second information;
adjusting, by the computer, parameters of the system using the third information;
generating, by the biological reader, one or more images of the biological growth plate using the biological reader, the one or more images including the first image; and
processing, by the computer, the one or more images using the selected imaging processing profile.

5. The method of claim 3, wherein the manufacturing information includes: fourth information indicative of a manufacturing date associated with the biological growth plate.

6. The method of claim 5, further comprising:
determining, by the computer, an expiration date associated with the biological growth plate using the manufacturing date; and
identifying, by the computer, the biological growth plate as expired if the expiration date has passed.

7. The method of claim 1, further comprising:
incubating, by an incubator of the system, the biological growth plate;
recording, by the computer, times associated with inoculating, incubating and generating the image; and
associating, by the computer, the times with the identification element.

8. The method of claim 1, wherein the biological growth plate comprises a hydrogel.

9. The method of claim 1, further comprising adjusting, by the computer, based on the manufacturing information, a parameter used to generate the image of the biological growth plate.

10. The method of claim 9, wherein the parameter is selected from the group consisting of an illumination source, an illumination angle, and a camera exposure.

11. The method of claim 1, further comprising adjusting, by the computer, based on the manufacturing information, an algorithm used to count the bacterial colonies.

12. The method of claim 1, further comprising:
after identifying the manufacturing information, providing, by the system, a dwell time for gelling the biological growth plate, wherein the manufacturing information is used to direct the dwell time.

13. A method comprising:
reading, by an identification element reader of a biological growth medium processing system, an identification element associated with a biological growth plate on which bacterial colonies have formed, wherein the biological growth plate is obtained from a particular manufacturing lot;
identifying, by a computer of the system, manufacturing information associated with the particular manufacturing lot using the identification element;
wherein the manufacturing information includes one or more spectroscopy measurements measured from the biological growth plate when the biological growth plate was manufactured;
identifying, by the computer, based on the spectroscopy measurements, variations from expected colors;
generating, by a biological reader of the system, an image of the biological growth plate;
modifying, by the computer, the image by applying color offsets to colors of the image of the biological growth plate, thereby accounting for the variations from the expected colors; and
counting, by the computer, using the modified image, the bacterial colonies on the biological growth plate.

* * * * *